US00PP32331P3

(12) United States Plant Patent
van Langen

(10) Patent No.: US PP32,331 P3
(45) Date of Patent: Oct. 13, 2020

(54) ***ECHEVERIA* PLANT NAMED 'TSAECH1812'**

(50) Latin Name: ***Echeveria* hybrid**
Varietal Denomination: TSAECH1812

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 16/602,742

(22) Filed: Dec. 2, 2019

(65) Prior Publication Data

US 2020/0178450 P1 Jun. 4, 2020

(51) Int. Cl.
*A01H 5/12* (2018.01)
*A01H 6/32* (2018.01)
*A01H 6/00* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
See application file for complete search history.

*Primary Examiner* — Susan McCormick Ewoldt
(74) *Attorney, Agent, or Firm* — Samuel R. McCoy, Jr.

(57) ABSTRACT

A new and distinct *Echeveria* plant named 'TSAECH1812' which is characterized by succulent foliage which is somewhat loosely held in a compact stemless rosette, lightly glaucous, dark yellow-green and greyed-green foliage which is distally margined and tipped greyed-red, and the stability of these characteristics from generation to generation.

3 Drawing Sheets

Latin name of the genus and species: The Latin name of the genus and species of the novel variety disclosed herein is *Echeveria* hybrid.

Variety denomination: The inventive variety of *Echeveria* disclosed herein has been given the variety denomination 'TSAECH1812'.

BACKGROUND OF THE INVENTION

Parentage: 'TSAECH1812' is a seedling selection resulting from the controlled pollination of an unnamed *Echeveria affinis* plant (not patented), the seed parent, with *Echeveria* hybrid 'Perle von Nurnberg' (not patented), the pollen parent. The crossing was made by the inventor in the spring of 2015 at a commercial greenhouse in Heerhugowaard, the Netherlands. In the spring of 2016, one seedling resulting from the cross of 2015 was observed to exhibit unique growth and foliage characteristics and was isolated for further evaluation in order to confirm the distinctness and stability of the characteristics first observed. Upon confirmation of distinctness and stability, 'TSAECH1812' was selected for commercialization.

Asexual Reproduction: Asexual reproduction of the new cultivar 'TSAECH1812', by way of rooting leaf cuttings, was first initiated in the spring of 2017 at the inventor's commercial greenhouse in Heerhugowaard, the Netherlands. Through three subsequent generations, the unique features of this cultivar have proven to be stable and true to type.

SUMMARY OF THE INVENTION

The cultivar 'TSAECH1812' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1812'. These characteristics in combination distinguish 'TSAECH1812' as a new and distinct *Echeveria* cultivar:

1. 'TSAECH1812' exhibits broad succulent foliage which is somewhat loosely held in a stemless rosette; and
2. 'TSAECH1812' exhibits glaucous, dark yellow-green and greyed-green foliage with light greyed-red suffusion which gives the foliage a somewhat beige appearance; and
3. 'TSAECH1812' exhibits foliage that is margined and tipped greyed-red.

BOTANICAL DESCRIPTION OF THE PLANT

Figure 1:
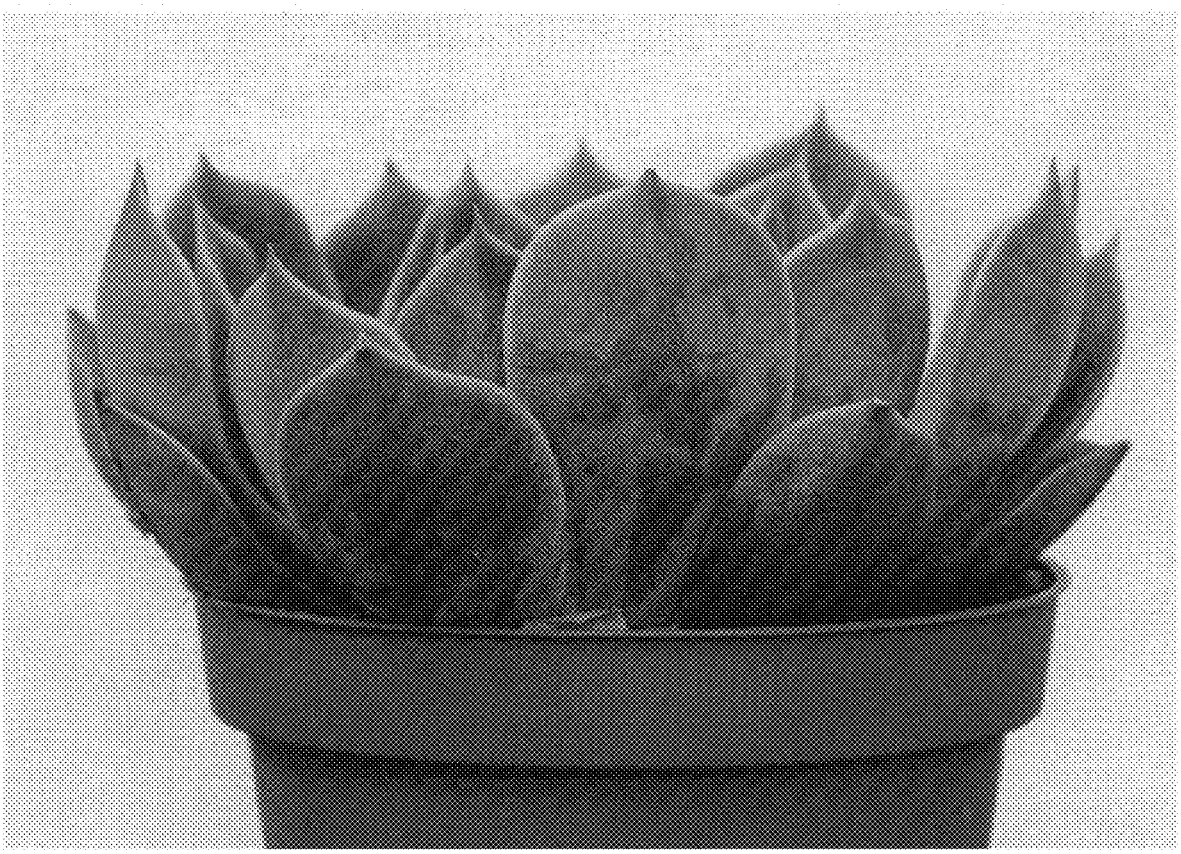
FIG. 1 illustrates, as nearly true as it is reasonably possible to make the same in color photographs of this type, an exemplary plant of 'TSAECH1812' grown in a commercial greenhouse in Heerhugowaard, the Netherlands. This plant is approximately 12 months old, shown planted in a 12 cm container.
Figure 2:
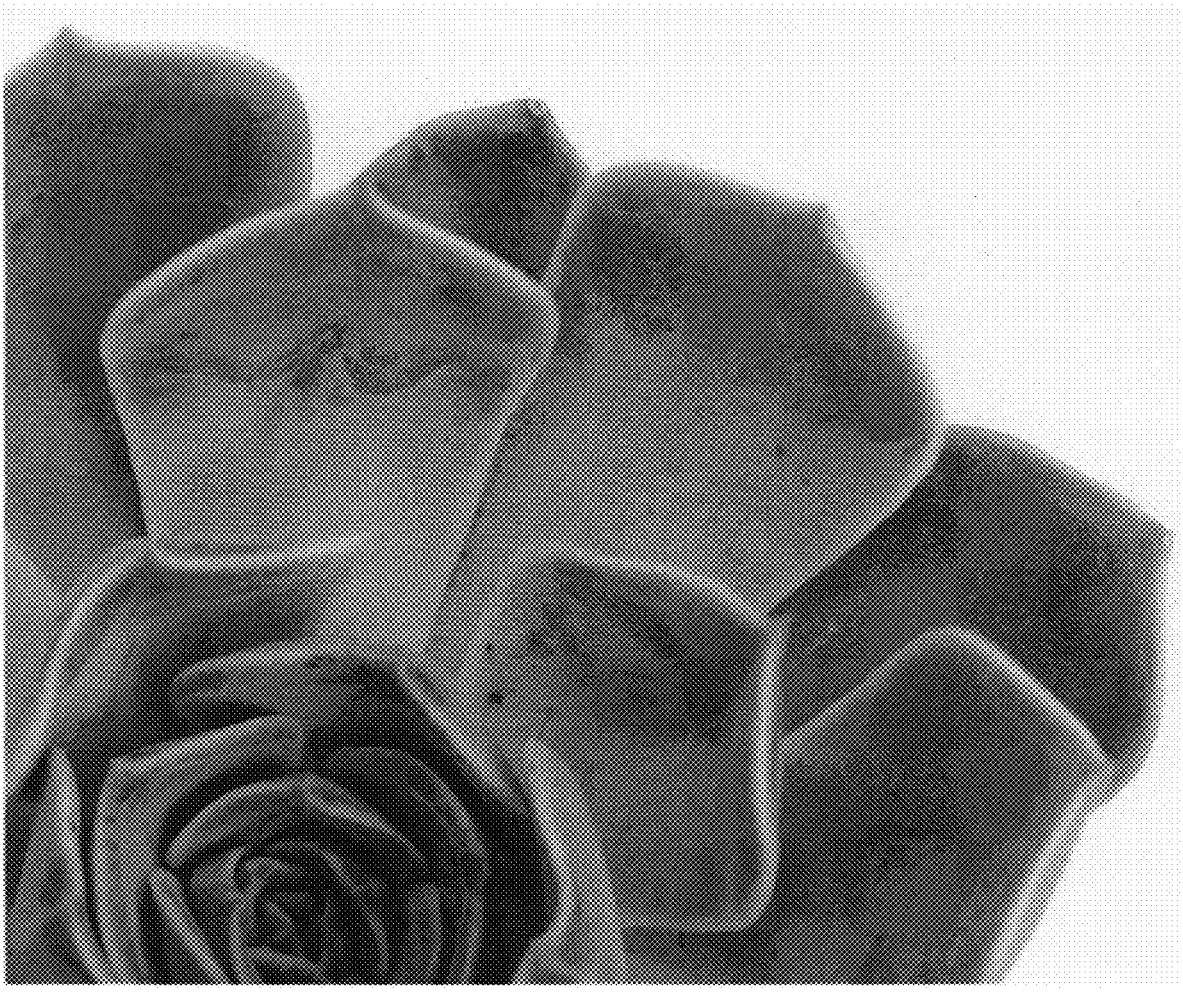
FIG. 2 illustrates, as nearly true as it is reasonably possible to make the same in color photographs of this type, the adaxial surface of the juvenile and mature foliage of 'TSAECH1812'.
Figure 3:
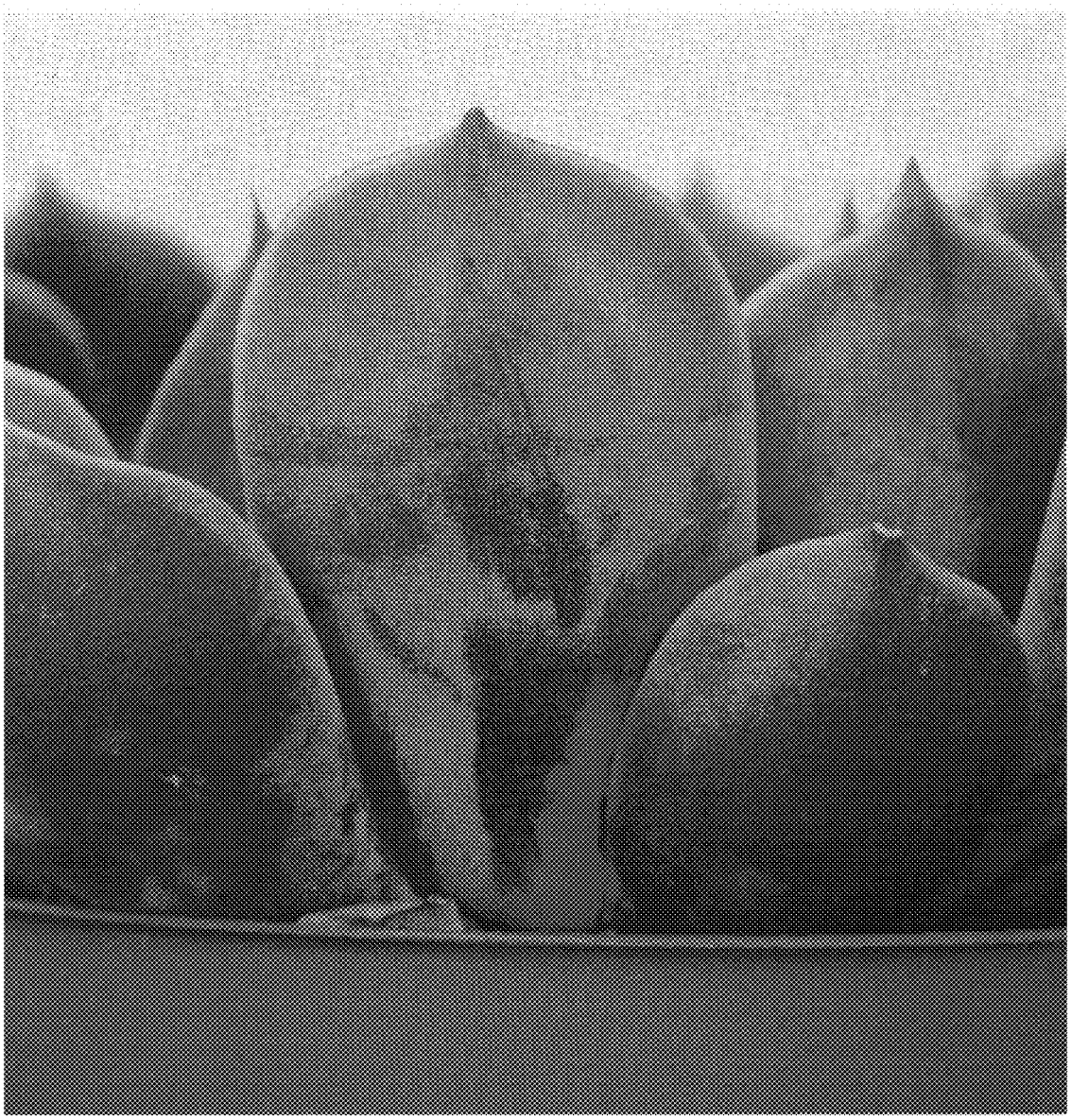
FIG. 3 illustrates, as nearly true as it is reasonably possible to make the same in color photographs of this type, the abaxial surface of the mature foliage of 'TSAECH1812'.

The following observations and measurements made in July of 2019 describe averages from a sample set of six specimens of 12 months old 'TSAECH1812' plants grown in 10.5 cm nursery containers at commercial greenhouse in Heerhugowaard, the Netherlands. Plants were produced using conventional greenhouse production protocols for

*Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1812' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'TSAECH1812' and comparisons with the parent plants and closest known comparator are provided below.

Plant description:

*Growth habit*.—Succulent perennial with foliage growing in a stemless basal rosette.

*Plant shape*.—Flattened.

*Height from soil level to top of foliar plane*.—6.0 cm.

*Plant spread*.—Average of 13.1 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in a 10.5 cm container.

*Disease and pest resistance or susceptibility*.—More resistant to insect pests known to infest *Echeveria* spp.; no more or less tolerant or resistant to pathogens known to infect *Echeveria* spp.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Foliage:

*Arrangement*.—Rosette.

*Division*.—Simple.

*Attachment*.—Sessile.

*Quantity*.—Approximately 36 leaves per rosette.

*Shape*.—Narrow obovate to broad oblanceolate.

*Dimensions*.—7.5 cm long, 3.2 cm wide, and 0.6 cm thick, on average.

*Aspect*.—Moderately concave and slightly curved upwards.

*Attitude*.—Both juvenile and mature foliage are held upright at an average angle of 30 degrees from vertical; outermost whorls are slightly more relaxed.

*Apex*.—Apiculate.

*Base*.—Long cuneate.

*Margin*.—Entire; not undulated.

*Pubescence, texture and luster of the adaxial surface*.—Glabrous, smooth, and matte; glaucous.

*Pubescence, texture and luster of the abaxial surface*.—Glabrous, smooth, and matte; glaucous.

*Color*.—Juvenile foliage, adaxial surface — Greyed-green, nearest to RHS 189A, and suffused with a darker yellow-green towards the apex, nearest to in between RHS 147A and 147B; fading to a lighter shade of yellow-green towards the base, nearest to RHS 147D; margined greyed-green, nearest to RHS 193B; tipped greyed-red, nearest to in between 179B and 179C; the epicuticular wax covering the leaf surface is greyed-green, nearest to in between RHS 188B and 188C. Juvenile foliage, abaxial surface — Yellow-green, nearest RHS N138C, and fading to a lighter shade of yellow-green towards the base, nearest to RHS 147D; margined greyed-green, nearest to RHS 193B; tipped greyed-red, nearest to RHS 179B; the epicuticular wax covering the leaf surface is greyed-green, nearest to RHS N189D. Mature foliage, adaxial surface — Nearest to in between yellow-green and greyed-green, RHS 147B and 191A, and fading to a lighter shade of yellow-green towards the base, nearest to RHS 148D; margined greyed-orange, nearest to in between RHS N170C and N170D; tipped greyed-red, nearest to RHS 180B; the epicuticular wax covering the leaf surface is greyed-green, nearest to in between RHS 188B and 188C. Mature foliage, abaxial surface — Greyed-green, nearest to RHS 197A, and suffused with a darker shade of greyed-green towards the base, nearest to RHS 194A; becoming a lighter shade of yellow-green at the base, nearest to RHS 147D; suffused with greyed-red, nearest to RHS 181B; margined greyed-orange, nearest to in between RHS N170C and N170D; tipped greyed-red, nearest to RHS 180A; the epicuticular wax covering the leaf surface is greyed-green, nearest to RHS N189D.

*Venation*.—No venation is visible.

*Petiole*.—No petiole; leaves are sessile.

Inflorescence: No flowering has been observed to date.

Comparisons with the parent plant and closest known comparator: Plants of the new cultivar 'TSAECH1812' differ from the seed parent, an unnamed and unpatented *Echeveria affinis* plant, in the following characteristics described in Table 1 below.

TABLE 1

| Characteristic | 'TSAECH1812' | *Echeveria affinis* seed parent. |
|---|---|---|
| Plant size. | Larger than the seed parent. | Smaller than 'TSAECH1812'. |
| Foliage size. | Larger than the seed parent. | Smaller than 'TSAECH1812'. |
| General coloration of the foliage. | A darker shade of greyed-green. | A lighter shade of greyed-green. |
| General coloration of the mature foliage. | Dark yellow green with light greyed-red suffusion creates a beige appearance; margined and tipped pink. | Yellow-green and heavily suffused with black; mature foliage is margined red. |
| Resistance to insect pests. | Not as resistant to insect pests. | Not as resistant to insect pests. |

Plants of the new cultivar 'TSAECH1812' differ from the pollen parent, *Echeveria* hybrid 'Perle von Nurnberg' (not patented), in the following characteristics described in Table 2 below.

TABLE 2

| Characteristic | 'TSAECH1812' | 'Perle von Nurnberg' |
|---|---|---|
| Plant profile. | Flattened. | Globular. |
| Foliage arrangement. | More loosely whorled. | More tightly whorled. |
| Foliage width. | Narrower than 'Perle von Nurnberg'. | Broader than 'TSAECH1812'. |
| General coloration of the foliage. | Dark yellow green with light greyed-red suffusion creates a beige appearance; margined and tipped pink. | In between blue-grey and blue-green. |

Comparisons with the closest known comparator: Plants of the new cultivar 'TSAECH1812' differ from the closest known commercial comparator, the common form of the species *Echeveria lilacina* (not patented), in the following characteristics described in Table 3 below.

TABLE 3

| Characteristic | 'TSAECH1812' | '*Echeveria lilacina*' |
|---|---|---|
| General coloration of the foliage | Dark yellow green with light greyed-red suffusion creates a beige appearance; margined and tipped greyed-red. | Very light grey, almost white, with lilac hues. |

That which is claimed is:

1. A new and distinct variety of *Echeveria* plant named 'TSAECH1812', substantially as described and illustrated herein.

* * * * *